(12) United States Patent
Indo et al.

(10) Patent No.: US 9,347,314 B2
(45) Date of Patent: May 24, 2016

(54) SYSTEM AND METHOD FOR QUANTIFYING UNCERTAINTY OF PREDICTED PETROLEUM FLUID PROPERTIES

(71) Applicant: Schlumberger Technology Corporation, Sugar Land, TX (US)

(72) Inventors: Kentaro Indo, Sugar Land, TX (US); Kai Hsu, Sugar Land, TX (US); Julian Pop, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 250 days.

(21) Appl. No.: 13/912,920

(22) Filed: Jun. 7, 2013

(65) Prior Publication Data

US 2014/0360259 A1 Dec. 11, 2014

(51) Int. Cl.
| | |
|---|---|
| *E21B 49/08* | (2006.01) |
| *E21B 47/10* | (2012.01) |
| *G01N 21/31* | (2006.01) |
| *G06F 1/32* | (2006.01) |

(52) U.S. Cl.
CPC ............ *E21B 49/088* (2013.01); *E21B 47/102* (2013.01); *G01N 21/31* (2013.01); *G06F 1/3203* (2013.01)

(58) Field of Classification Search
None
See application file for complete search history.

(56) References Cited

U.S. PATENT DOCUMENTS

| | | | |
|---|---|---|---|
| 6,768,105 B2 | 7/2004 | Mullins et al. | |
| 7,095,012 B2 | 8/2006 | Fujisawa et al. | |
| 7,305,306 B2 | 12/2007 | Venkataramanan et al. | |
| 7,336,356 B2 | 2/2008 | Vannuffelen et al. | |
| 7,379,180 B2 | 5/2008 | Vannuffelen et al. | |
| 7,389,159 B2 | 6/2008 | Warren et al. | |
| 7,428,925 B2 | 9/2008 | Brown et al. | |
| 7,644,610 B2 | 1/2010 | Meister | |
| 7,966,273 B2 | 6/2011 | Hegeman et al. | |
| 7,996,153 B2 | 8/2011 | Niemeyer et al. | |
| 8,024,125 B2 | 9/2011 | Hsu et al. | |
| 8,068,226 B2 | 11/2011 | Csutak | |
| 8,146,415 B2 | 4/2012 | Cartellieri | |
| 2003/0048450 A1* | 3/2003 | Pope et al. | 356/435 |
| 2006/0155472 A1* | 7/2006 | Venkataramanan | E21B 49/00 702/10 |

(Continued)

FOREIGN PATENT DOCUMENTS

WO 2012108886 A1 8/2012

OTHER PUBLICATIONS

B. Efron, "Bootstrap methods: Another look at the Jackknife" The Annals of Statistics (1979), vol. 7, No. 1, 1-26.

(Continued)

*Primary Examiner* — Andre Allen
(74) *Attorney, Agent, or Firm* — Kenneth L. Kincaid

(57) ABSTRACT

A system includes a downhole formation fluid sampling tool. The system also includes an optical spectrometer of the downhole formation fluid sampling tool and a processor. The optical spectrometer is able to measure an optical characteristic of a formation fluid flowing through the downhole formation fluid sampling tool over a plurality of wavelengths. The optical spectrometer is designed to generate optical spectra data indicative of the optical characteristic. The processor is able to receive the optical spectra data generated by the optical spectrometer, to predict a parameter corresponding to one component of multiple components of the formation fluid based on the optical spectra data, and to calculate an uncertainty in the predicted parameter based on the optical spectra data.

20 Claims, 7 Drawing Sheets

(56) References Cited

U.S. PATENT DOCUMENTS

| | | | |
|---|---|---|---|
| 2006/0155474 A1* | 7/2006 | Venkataramanan | E21B 49/00 702/13 |
| 2007/0119244 A1 | 5/2007 | Goodwin et al. | |
| 2009/0030858 A1 | 1/2009 | Hegeman et al. | |
| 2009/0288881 A1 | 11/2009 | Mullins et al. | |
| 2009/0321072 A1* | 12/2009 | Kanayama et al. | 166/250.01 |
| 2011/0048700 A1 | 3/2011 | Van Zuilekom et al. | |
| 2011/0088895 A1* | 4/2011 | Pop et al. | 166/254.2 |
| 2011/0218736 A1 | 9/2011 | Pelletier | |
| 2011/0284219 A1* | 11/2011 | Pomerantz et al. | 166/264 |
| 2012/0018152 A1 | 1/2012 | Zuilekom et al. | |
| 2014/0096955 A1* | 4/2014 | Indo et al. | 166/250.01 |
| 2014/0138528 A1* | 5/2014 | Pope et al. | 250/269.1 |
| 2014/0150545 A1* | 6/2014 | Hsu et al. | 73/152.24 |
| 2014/0180591 A1* | 6/2014 | Hsu et al. | 702/8 |
| 2014/0238670 A1* | 8/2014 | Pop et al. | 166/264 |
| 2014/0278113 A1* | 9/2014 | Chok | E21B 49/088 702/13 |
| 2014/0360257 A1* | 12/2014 | Indo et al. | 73/152.28 |
| 2015/0054512 A1* | 2/2015 | DiFoggio | 324/324 |

OTHER PUBLICATIONS

Hegeman, P., Dong, C., Varotsis, N., and Gaganis, V.: "Application of Artificial Neural Networks to Downhole Fluid Analysis," paper IPTC 11268 PP, presented at the International Petroleum Technology Conference, Dubai, U.A.E., Dec. 2007; published SPEREE (Feb. 2009) as SPE 123423.

Robert A. Stine, "Bootstrap Prediction Intervals for Regression", Journal of the American Statistical Association, vol. 80, No. 392 (Dec. 1985), pp. 1026-1031.

U.S. Appl. No. 13/644,772, "Determining Fluid Composition Downhole From Optical Spectra".

Fujisawa, G.; Mullins, O.; Dong, C.; Carnegie, A.; Betancourt, S.; Terabayashi, T.; Yoshida, S.; Jaramillo, A. and Haggag, M., "Analyzing Reservoir Fluid Composition In-Situ in Real Time: Case Study in a Carbonate Reservoir", Society of Petroleum Engineers, SPE 84092, presented at the SPE Annual Technical Conference and Exhibition held in Denver, Colorado, U.S.A., Oct. 5-8, 2003, pp. 1-9.

Venkataramanan, L.; Elshahawi, H.; McKinney D.; Flannery, M. and Hashem, M., "Downhole Fluid Analysis and Fluid Comparison Algorithm as an Aid to Reservoir Characterization", Society of Petroleum Engineers, SPE 100937, presented at the 2006 SPE Asia Pacific Oil & Gas Conference and Exhibition held in Adelaide, Australia, Sep. 11-13, 2006, pp. 1-16.

Dong, C.; O'Keefe, M.; Elshahawi, H.; Hashem, M.; Williams, S.; Stensland, D.; Hegeman, P.; Vasques, R; Terabayashi, T.; Mullins, O. and Donzier, E., "New Downhole-Fluid-Analysis Tool for Improved Reservoir Characterization", Society of Petroleum Engineers, SPE 108566, presented at Offshore Europe, Aberdeen, Sep. 4-7, 2008, pp. 1107-1116.

International Patent Application Serial No. PCT/US2013/030637, "Method and Apparatus for Identifying Fluid Attributes".

International Search Report and the Written Opinion for International Application No. PCT/US2014/041364 dated Oct. 13, 2014.

* cited by examiner

SYSTEM AND METHOD FOR QUANTIFYING UNCERTAINTY OF PREDICTED PETROLEUM FLUID PROPERTIES

BACKGROUND

The present disclosure relates generally to drilling systems and more particularly to tools for sampling and analyzing formation fluid.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Wells are generally drilled into a surface (land-based) location or ocean bed to recover natural deposits of oil and gas, as well as other natural resources that are trapped in geological formations in the Earth's crust. A well is often drilled using a drill bit attached to the lower end of a "drill string," which includes drillpipe, a bottom hole assembly, and other components that facilitate turning the drill bit to create a borehole. Drilling fluid, or "mud," is pumped down through the drill string to the drill bit during a drilling operation. The drilling fluid lubricates and cools the drill bit, and it carries drill cuttings back to the surface in an annulus between the drill string and the borehole wall.

Information about the subsurface formations, such as measurements of the formation pressure, formation permeability and the recovery of formation fluid samples may be useful for predicting the economic value, the production capacity, and production lifetime of a subsurface formation. Downhole tools, such as formation testers, may perform evaluations in real-time during sampling of the formation fluid. For example, a downhole formation fluid sampling tool can include an onboard spectrometer to measure optical characteristics of the formation fluid flowing through the sampling tool. Such measurements are often used to determine when the formation fluid flowing through the downhole tool is ready to be sampled. However, the measurements may also be used to predict some physical and chemical properties of the formation fluid, such as hydrocarbon composition, carbon dioxide composition, and GOR, among others. Such real-time predictions can include uncertainties due to measurement noise.

SUMMARY

In a first embodiment, a system includes a downhole formation fluid sampling tool. The system also includes an optical spectrometer of the downhole formation fluid sampling tool and a processor. The optical spectrometer is able to measure an optical characteristic of a formation fluid flowing through the downhole formation fluid sampling tool over a plurality of wavelengths. The optical spectrometer is designed to generate optical spectra data indicative of the optical characteristic. The processor is able to receive the optical spectra data generated by the optical spectrometer, to predict a parameter corresponding to one component of multiple components of the formation fluid based on the optical spectra data, and to calculate an uncertainty associated with the predicted parameter based on the optical spectra data.

In another embodiment, a method includes receiving optical spectra data into a processor. The optical spectra data is representative of optical characteristics of a formation fluid flowing through a downhole formation fluid sampling tool. The method also includes predicting, via the processor, a parameter corresponding to one component of multiple components of the formation fluid based on the optical spectra data. In addition, the method includes determining, via the processor, an uncertainty in the predicted parameter corresponding to the one component of the multiple components of the formation fluid based on the optical spectra data.

In a further embodiment, a method includes receiving optical spectra data into a processor. The optical spectra data is representative of optical characteristics of a formation fluid flowing through the downhole formation fluid sampling tool. The method also includes predicting, via the processor, a parameter corresponding to components of the formation fluid based on the optical spectra data and a model derived from a calibration dataset. In addition, the method includes determining, via the processor, a measurement uncertainty in the received optical spectra data. Further, the method includes identifying, via the processor, a model uncertainty in the model derived from the calibration dataset. Still further, the method includes determining, via the processor, an uncertainty in the predicted parameter based on the measurement uncertainty and the model uncertainty.

Various refinements of the features noted above may exist in relation to various aspects of the present disclosure. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

Figure 1:
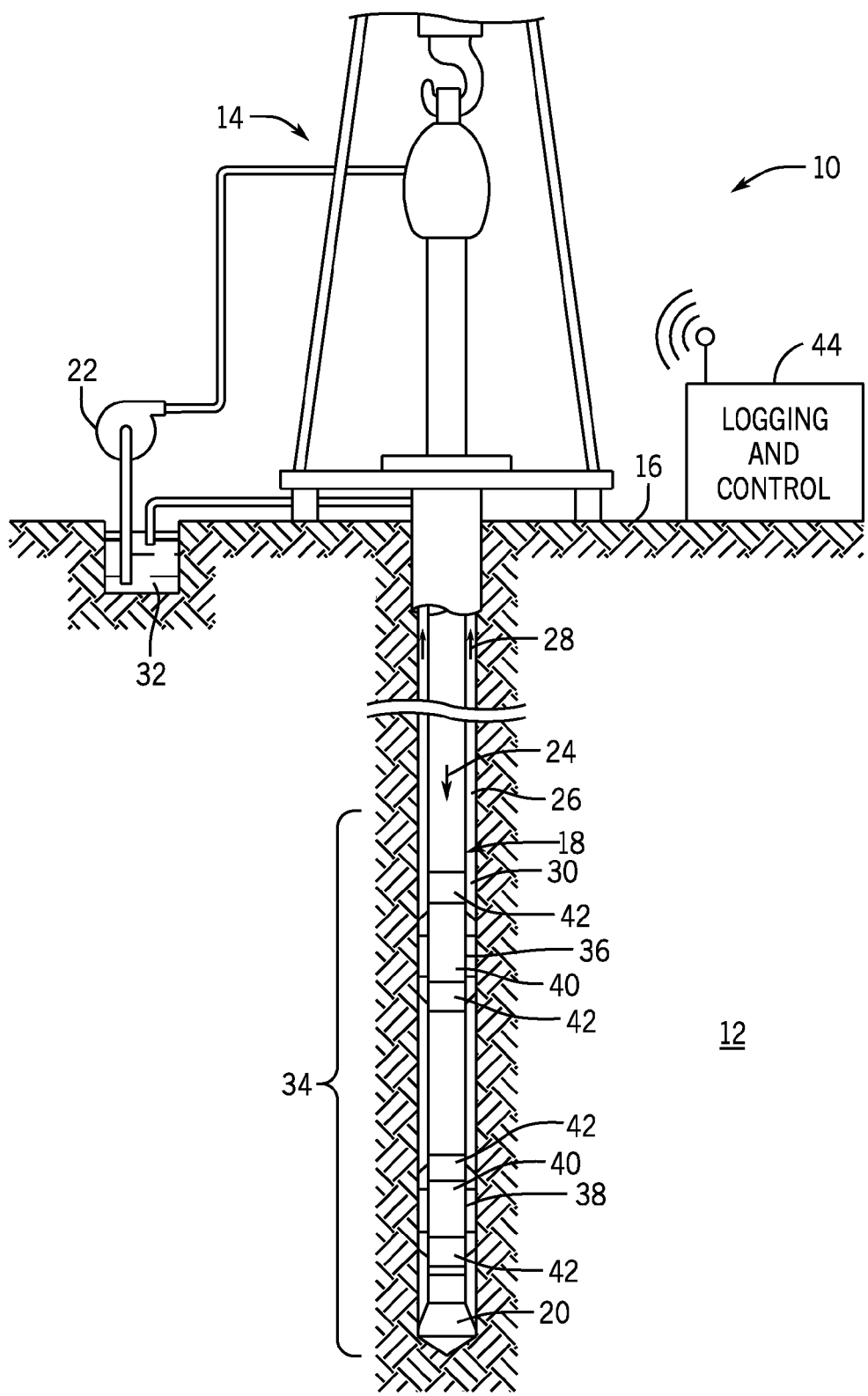
FIG. 1 is a schematic representation including a partial cross sectional view of a drilling system used to drill a well through subsurface formations, in accordance with an embodiment of the present techniques.

One or more specific embodiments of the present disclosure will be described below. These described embodiments are examples of the presently disclosed techniques. Additionally, in an effort to provide a concise description of these embodiments, features of an actual implementation may not be described in the specification. It should be appreciated that in the development of any such actual implementation, as in any engineering or design project, numerous implementation-specific decisions can be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Present embodiments are directed to systems and methods for quantifying an uncertainty in predicted parameters of a formation fluid sampled via a formation fluid sampling tool configured for operation downhole. Specifically, such parameters are predicted based on optical spectra data of the formation fluid as it flows through the downhole tool. The optical spectra data is generated via an optical spectrometer of the downhole tool. One or more processors, which may be present in the downhole tool or located at a surface of the well, perform the prediction and calculate an uncertainty of the prediction based in part on the optical spectra data obtained via the spectrometer. The predicted parameter may correspond to one component (e.g., hydrocarbon component, carbon dioxide) of multiple components that make up the formation fluid. The processor may determine the uncertainty in the predicted parameter for the one component, and propagate the uncertainty to an aggregate parameter of the formation fluid. In some embodiments, the processor may predict the parameter by fitting the optical spectra data to a model derived from a calibration dataset. In such instances, the processor may determine the uncertainty in the predicted parameter based on a measurement uncertainty and a model uncertainty. The measurement uncertainty, which relates to measurement noise, may be determined based on the optical spectra data. The model uncertainty, which relates to errors in the model, may be derived from the calibration dataset.

FIG. 1 illustrates a drilling system 10 used to drill a well through subsurface formations 12. A drilling rig 14 at the surface 16 is used to rotate a drill string 18 that includes a drill bit 20 at its lower end. As the drill bit 20 is rotated, a "mud" pump 22 is used to pump drilling fluid, commonly referred to as "mud" or "drilling mud," downward through the center of the drill string 18 in the direction of the arrow 24 to the drill bit 20. The mud, which is used to cool and lubricate the drill bit 20, exits the drill string 18 through ports (not shown) in the drill bit 20. The mud then carries drill cuttings away from the bottom of a borehole 26 as it flows back to the surface 16, as shown by the arrows 28 through an annulus 30 between the drill string 18 and the formation 12. At the surface 16, the return mud is filtered and conveyed back to a mud pit 32 for reuse.

While a drill string 18 is illustrated in FIG. 1, it will be understood that the embodiments described herein are applicable to work strings and wireline tools as well. Work strings may include a length of tubing (e.g. coil tubing) lowered into the well for conveying well treatments or well servicing equipment. Wireline tools may include formation testing tools suspended from a multi-wire cable as the cable is lowered into a well so that it can measure formation properties at desired depths. It should be noted that the location and environment of the well may vary widely depending on the formation 12 into which it is drilled. Instead of being a surface operation, for example, the well may be formed under water of varying depths, such as on an ocean bottom surface. Certain components of the drilling system 10 may be specially adapted for underwater wells in such instances.

As illustrated in FIG. 1, the lower end of the drill string 18 includes a bottom-hole assembly ("BHA") 34 that includes the drill bit 20, as well as a plurality of drill collars 36, 38. The drill collars 36, 38 may include various instruments, such as sample-while-drilling ("SWD") tools that include sensors, telemetry equipment, and so forth. For example, the drill collars 36, 38 may include logging-while-drilling ("LWD") modules 40 and/or measurement-while drilling ("MWD") modules 42. The LWD modules or tools 40 may include tools configured to measure formation parameters or properties, such as resistivity, porosity, permeability, sonic velocity, and so forth. The MWD modules or tools 42 may include tools configured to measure wellbore trajectory, borehole temperature, borehole pressure, and so forth. The LWD modules 40 of FIG. 1 are each housed in one of the drill collars 36, 38, and each contain any number of logging tools and/or fluid sampling devices. The LWD modules 40 include capabilities for measuring, processing and/or storing information, as well as for communicating with the MWD modules 42 and/or directly with the surface equipment such as, for example, a logging and control unit 44. That is, in some embodiments, the SWD tools (e.g., LWD and MWD modules 40, 42) may be communicatively coupled to the logging and control unit 44 disposed at the surface 16. In other embodiments, portions of the logging and control unit 44 may be integrated with downhole features.

The LWD modules 40 and/or the MWD modules 42 may include a downhole fluid formation sampling tool configured to sample formation fluid. In presently disclosed embodiments, the drilling system 10 may be capable of predicting certain properties associated with the sampled formation fluid. These properties may include an estimated composition of the formation fluid sampled by the downhole tool, and other properties derived from the composition. In addition to predicting such properties, the drilling system 10 may determine a quantitative uncertainty for each of the predicted formation fluid properties. Such predictions, in combination with their associated uncertainties, may be used within the tool to control tool operations or may be determined within or communicated to the logging and control unit 44, and used as inputs to various control functions and/or data displays (for example, monitors and logs).

Figure 2:
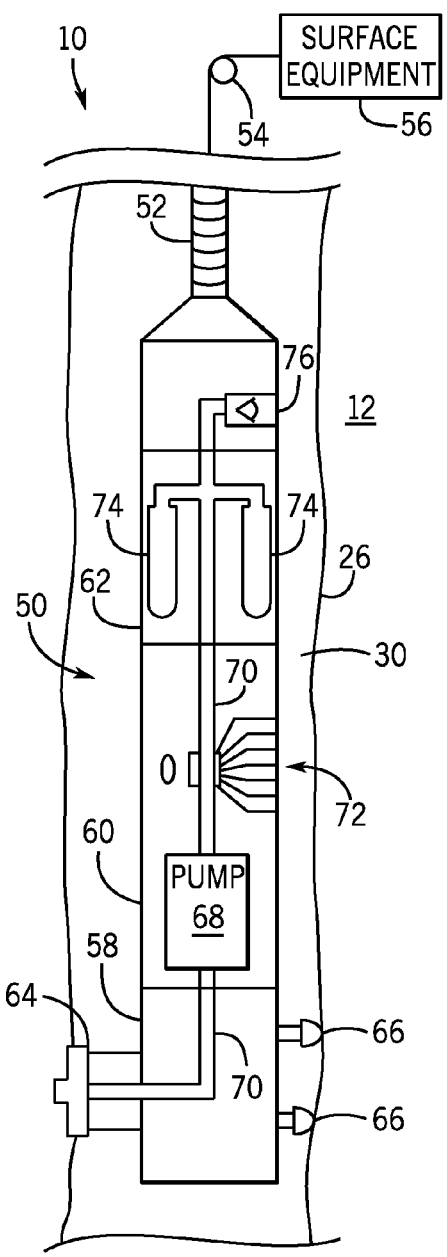
FIG. 2 is a schematic diagram of downhole equipment used to sample a subsurface formation, in accordance with an embodiment of the present techniques.

FIG. 2 is a schematic diagram of an embodiment of downhole equipment (equipment configured for operation downhole) used to sample a well formation. Specifically, the illustrated downhole equipment includes an embodiment of a downhole fluid formation sampling tool 50, hereinafter referred to as a downhole tool 50. The downhole tool 50 is illustrated as being disposed within the wellbore 26 of the subsurface formation 12 in order to sample formation fluid from the formation 12. In the illustrated embodiment, the downhole tool 50 is disposed in the wellbore 26 via a wireline 52. The downhole tool 50 may be suspended in the wellbore 26 from a lower end of the wireline 52, which may be a multi-conductor cable spooled, from a winch 54. The wireline 52 may be electrically coupled to surface equipment 56, in order to communicate various control signals and logging information between the downhole tool 50 and the surface equipment 56. It should be noted that in other embodiments, such as shown in FIG. 1, the downhole tool 50 may include one or more of the SWD tools, which are disposed in the wellbore 26 via the drill string 18.

The illustrated downhole tool 50 includes a probe module 58, a pumpout module 60, and a multi-sample module 62. It should be noted that other arrangements of the modules that make up the downhole tool 50 may be possible. Moreover, the different components shown within each of the illustrated modules may be arranged differently in other embodiments of the downhole tool 50.

The illustrated probe module 58 includes an extendable fluid communication line (probe 64) designed to engage the formation 12 and to communicate fluid samples from the formation 12 into the downhole tool 50. In addition to the probe 64, the illustrated probe module 58 includes two setting mechanisms 66. The setting mechanisms 66 may include pistons in some embodiments, although other types of probe modules 58 may utilize a different type of probe 64 and/or setting mechanism 66. For example, in some embodiments the probe module 58 may include one or more packer elements configured to be inflated to contact an inner wall of the wellbore 26, thereby isolating a section of the wellbore 26 for sampling. In addition, the probe module 58 may include electronics, batteries, sensors, and/or hydraulic components used to operate the probe 64 and the corresponding setting mechanisms 66.

The pumpout module 60 may include a pump 68 used to create a pressure differential that draws the formation fluid in through the probe 64 and pushes the fluid through a flowline 70 of the downhole tool 50. The pump 68 may include an electromechanical pump used for pumping formation fluid from the probe module 58 to the multi-sample module 62 and/or out of the downhole tool 50. In an embodiment, the pump 68 operates as a piston displacement unit (DU) driven by a ball screw coupled to a gearbox and an electric motor, although other types of pumps 68 may be possible as well. Power may be supplied to the pump 68 via other components located in the pumpout module 60, or via a separate power generation module (not shown). During a sampling process, the pump 68 moves the formation fluid through the flowline 70, toward the multi-sample module 62.

In addition to the pump 68, the illustrated pumpout module 60 includes an optical spectrometer 72 configured to measure an optical characteristic of the formation fluid as it flows through the flowline 70 toward the multi-sample module 62. The optical characteristic sensed by the spectrometer 72 may include optical density of the formation fluid, or any other desirable optical characteristic that may be used for predicting formation fluid properties. Optical data collected via the spectrometer 72 may be used to control the downhole tool 50. For example, the downhole tool 50 may not operate in a sample collection mode to collect fluid samples until the formation fluid flowing through the flowline 70 exhibits optical characteristics of a clean formation fluid sample, as detected by the spectrometer 72. A clean formation fluid sample contains a relatively low level of contaminants (e.g., drilling mud filtrate).

The multi-sample module 62 includes one or more sample bottles 74 for collecting samples of the formation fluid. Based on the optical density, or other sensed characteristics, of the formation fluid detected via sensors (e.g., spectrometer 72) along the flowline 70, the downhole tool 50 may be operated in a sample collection mode or a continuous pumping mode. When operated in the sample collection mode, valves disposed at or near entrances of the sample bottles 74 may be positioned to allow the formation fluid to flow into the sample bottles 74. The sample bottles 74 may be filled one at a time, and once a sample bottle 74 is filled, its corresponding valve may be moved to another position to seal the sample bottle 74. When the valves are closed, the downhole tool 50 may operate in a continuous pumping mode.

In a continuous pumping mode, the pump 68 moves the formation fluid into the downhole tool 50 through the probe 64, through the flowline 70, and out of the downhole tool 50 through an exit port 76. The exit port 76 may be a check valve that releases the formation fluid into the annulus 30 of the wellbore 26 or it may be a valve which performs a similar function but is operated by commands sent from the surface. The downhole tool 50 may operate in the continuous pumping mode until the formation fluid flowing through the flowline 70 is determined to be clean enough for sampling. This is because when the formation fluid is first sampled, residual drilling mud filtrate may enter the downhole tool 50 along with the sampled formation fluid. After pumping the formation fluid for an amount of time, the formation fluid flowing through the downhole tool 50 will provide a more pure sample of the uncontaminated formation fluid than would otherwise be available when first drawing fluid in through the probe 64. The formation fluid may be considered clean when the optical spectra data from the spectrometer 72 indicates that the formation fluid contains less than approximately 1% (by volume) drilling filtrate contamination.

Figure 3:
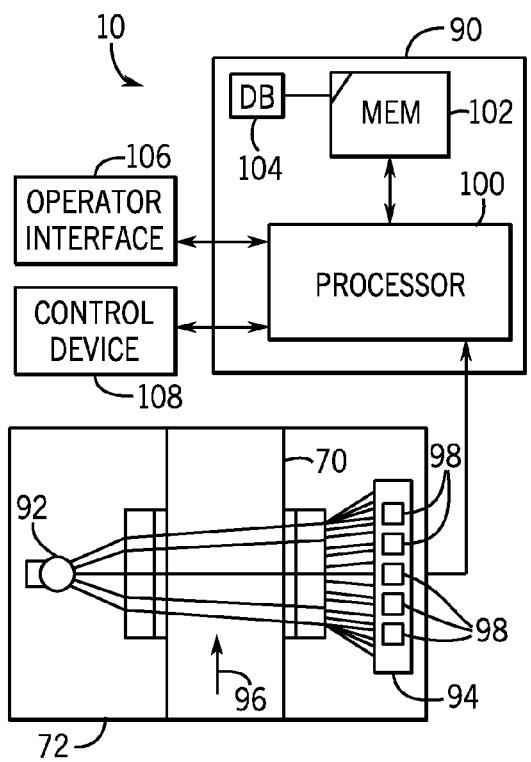
FIG. 3 is a schematic diagram of equipment used to predict formation fluid properties of formation fluid flowing through the downhole equipment of FIG. 2, in accordance with an embodiment of the present techniques.

The optical characteristics of the formation fluid measured by the spectrometer 72 may be useful for performing a variety of evaluation and control functions, in addition to determining when the formation fluid flowing through the flowline 70 is relatively clean for sample capture. For example, as discussed in detail below, the data collected from the spectrometer may be used to predict certain properties (e.g., composition, GOR) of the formation fluid and to estimate uncertainties associated with these predictions. FIG. 3 is a schematic diagram of equipment that may be used in the drilling system 10 to predict the formation fluid properties and their associated uncertainties. Such equipment, in the illustrated embodiment, includes the spectrometer 72 and a control/monitoring system 90.

The spectrometer 72 is shown in detail in the illustrated embodiment. The spectrometer 72 may include a light source 92 and a detector 94 disposed on opposite sides of the flowline 70 through which the formation fluid flows, as indicated by arrow 96. The spectrometer 72 may be part of the downhole tool 50, and may be located along any portion of the flowline 70 that directs the formation fluid through the downhole tool 50. Although a single light source 92 is shown, other embodiments of the spectrometer 72 may include additional light sources 92. The detector 94 may sense the light that passes through the formation fluid in the flowline 70.

The detector 94 may include multiple detector elements 98, each detector element 98 designed to measure the amount of light transmitted at a certain wavelength. For example, the detectors elements 98 may detect the light transmitted at 5, 10, 20, or more different wavelengths within a range of approximately 400 to 2200 nm. However, other numbers of wavelengths (corresponding to the number of detector elements) and other ranges of wavelengths may be possible. For example, in some embodiments it may be desirable to detect optical characteristics of the formation fluid at a relatively limited range of wavelengths, such as the near infrared (NIR) wavelength range of approximately 1500-2050 nm.

The spectrometer 72 may measure certain optical characteristics of the formation fluid flowing through the flowline 70, and output optical spectra data representative of the detected optical characteristics. In an embodiment, the optical characteristics may include optical density of the formation fluid at each of the detected wavelengths. Optical density is a logarithmic measurement relating the intensity of light emitted from the light source 92 to the intensity of light detected by the detector 94 at a certain wavelength. Optical density may be expressed according to the equation shown below:

$$OD_\lambda = -\log\left(\frac{I}{I_o}\right) \quad (1)$$

In equation 1, $I_o$ represents the light intensity emitted from the light source 92, and I represents the light intensity measured by the detector element 98 corresponding to the particular wavelength $\lambda$. When expressed in this manner, a measured optical density (OD) of 0 corresponds to 100% of light transmission through the formation fluid at that wavelength. Similarly, an OD of 1 corresponds to 10% light transmission through the formation fluid, and an OD of 2 corresponds to 1% light transmission. The higher the optical density of the formation fluid, the lower the amount of light that is transmitted through the formation fluid and detected by the detector 94.

The spectrometer 72 may send optical spectra data representative of the measured optical characteristics to a processor 100 of the control/monitoring system 90. The term "processor" refers to any number of processor components located about the drilling system 10. In some embodiments, for example, the processor 100 may include a single processor disposed onboard the downhole tool 50. In other embodiments, the processor 100 may be located within the surface equipment 56 of FIG. 2, or the logging and control unit 44 of FIG. 1. In still further embodiments, the processor 100 may include one or more processors located within the downhole tool 50 connected to one or more processors located in drilling equipment disposed at the surface 16 of the drilling system 10. Moreover, any desirable combination of processors may be considered part of the processor 100 in the following discussion. Similar terminology is applied with respect to the control/monitoring system 90 as well as a memory 102 of the control/monitoring system 90, meaning that the control/monitoring system 90 may include any number of processors communicatively coupled to each other and to memories located throughout the drilling system 10.

The control/monitoring system 90 may predict a parameter of the formation fluid based on the optical spectra data received from the spectrometer 72, and determine a quantitative estimation of uncertainty of the prediction. The predicted parameter may include, for example, a relative concentration of a particular component that makes up the formation fluid. To make such uncertainty calculations, as well as the predictions, the processor 100 may execute various instructions stored in the memory 102.

In some embodiments, the processor 100 may utilize a calibration dataset stored in a database 104 within the memory 102. This calibration dataset may include a record of optical spectra data and corresponding parameters of the formation fluid, or components thereof, acquired during prior formation fluid sampling operations using the downhole tool 50. The formation fluid parameters stored in the dataset may include results from laboratory tests performed on formation fluid previously sampled by the downhole tool 50. In some embodiments, the processor 100 may use information derived from the dataset to predict the formation fluid parameter based on expected results for the optical spectra data from prior formation fluid samples. As more samples are taken using the downhole tool 50, the dataset may be updated within the database 104 to reflect the additional calibration data, creating a more accurate prediction model as more samples are taken.

The processor 100 may be communicatively coupled with one or more operator interfaces 106 and/or control devices 108. The operator interface 106 may include displays of various forms (for example, logs) of predicted formation fluid properties and their associated uncertainties, which may be accessed by an operator. In addition, the operator interface 106 may alert an operator to any issues with the spectrometer 72, as identified based on the uncertainty measurements. The operator interface 106 may also notify an operator when there is a relatively high uncertainty for a prediction relied upon for certain decisions for mitigating drilling risk or for performing control functions. The control device 108 may include any device or portion of the drilling system 10 that receives control signals for operation based on the predicted properties of the formation fluid, and the associated uncertainty of the predictions. Such control devices 108 may implement changes in depth of the downhole tool 50 within the wellbore 26, adjustments to the pumping rate or pressure of the pump 68, and/or other control functions, based on the predicted formation fluid composition or GOR.

Figure 4:
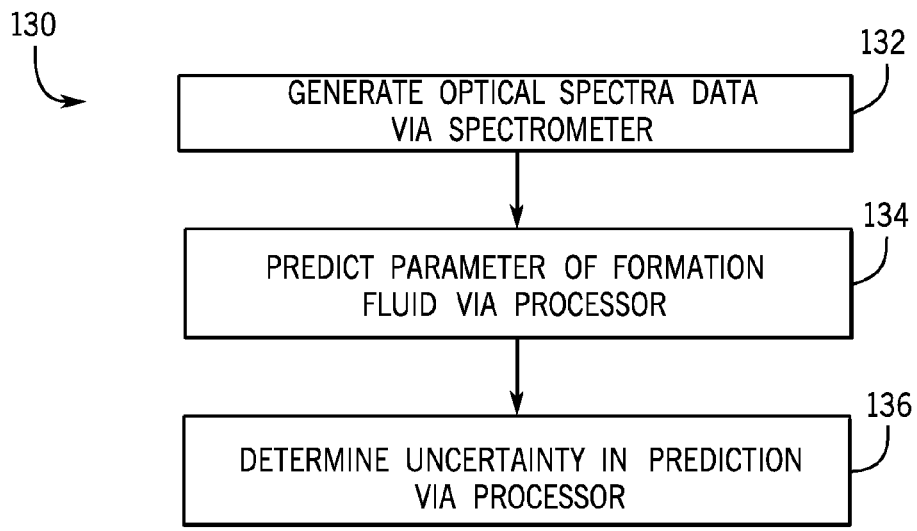
FIG. 4 is a process flow diagram of a method for performing predictions of properties of the formation fluid flowing through the downhole equipment of FIG. 2, in accordance with an embodiment of the present techniques.

FIG. 4 is a process flow diagram of a method 130 for performing predictions of properties of the formation fluid flowing through the downhole tool 50. It should be noted that the method 130 may be implemented as a computer or software program (e.g., code or instructions) that may be executed by the processor 100 to execute one or more parts of the method 130. Additionally, the program (e.g., code or instructions) may be stored in any suitable article of manufacture that includes at least one tangible non-transitory, computer-readable medium that at least collectively stores these instructions or routines, such as a memory or storage component of the control/monitoring system 90. The term non-transitory merely indicates that the medium is not a signal. Further, although the techniques are described herein with respect to determining properties of formation fluid flowing through a downhole tool 50, as may be appreciated, the techniques may be employed in other locations, such as at the surface or in a laboratory, among others. Moreover, the techniques described herein also may be employed to predict properties of other types of fluids.

The method 130 includes generating (block 132) optical spectra data associated with the formation fluid flowing through the downhole tool 50, via the spectrometer 72 of the downhole tool 50. Operation of the spectrometer 72 to generate the optical spectra data is described in detail above with reference to FIG. 3. In addition, the method 130 includes predicting (block 134) a parameter of the formation fluid via the processor 100. This prediction is based on the optical spectra data generated via the spectrometer 72. More specifically, the prediction may involve performing a linear transformation of the optical spectra data according to a mapping matrix. The mapping matrix may be derived from the calibration dataset stored in the database 104. The method 130 also includes determining (block 136) an uncertainty in the predicted parameter via the processor 100. In some embodiments, this uncertainty determination may involve identifying a covariance matrix of the mapping matrix, this covariance matrix being derived from the dataset of the database 104 as well.

The uncertainty may be a quantitative measure expressed as a confidence interval. The processor 100 may provide the prediction (with its determined uncertainty) to a log, operator interface 106, control device 108, or other components of the drilling system 10. Thus, such components may record, display, or implement controls based on a range of expected parameter values. Determining (block 136) such uncertainties may extend even to those parameters (e.g., relative concentration, composition by weight, etc.) for individual components within the formation fluid. These components may include various hydrocarbon groups C1, C2, C3, C4, C5, and C6+ and carbon dioxide (CO2). Predictions accompanied with such uncertainties may be more useful than predictions made using traditional systems, which generally provide a qualitative measure of the uncertainty. In addition, these traditional systems may provide the uncertainty corresponding to predicted parameters associated with the formation fluid as a whole, not with the individual components.

Having now discussed a general method for using optical spectra data to provide robust predictions of formation fluid parameters, a more detailed discussion of predicting (block 134) the parameters themselves will be provided. As noted above, the prediction may rely on a mapping of the optical spectra data obtained from the spectrometer 72. This mapping is shown in the equation below:

$$y = xB$$

$$x = [x(\lambda_1), x(\lambda_2), \ldots, x(\lambda_m)]$$

$$y = [y_{C1}, y_{C2}, y_{C3}, y_{C4}, y_{C5}, y_{C6+}, y_{CO2}] \quad (2)$$

In equation 2, $x(\lambda_m)$ and $y_i$, respectively, denote the optical spectra data (e.g., optical density measurement) at wavelength channel $\lambda_m$, and the predicted concentration of components i in the formation fluid. The formation fluid may be a crude oil, a gas condensate, or a gas. In an embodiment, y may be a relative concentration of each of the components C1, C2, C3, C4, C5, C6+ and CO2. The matrix B in equation 2 may represent a mapping matrix predetermined from the calibration dataset of the database 104. In some embodiments, a different mapping matrix B may be used when the formation fluid is identified as an oil, gas condensate, or gas. The mapping matrix B may be composed of column vectors associated with the individual formation fluid components as follows:

$$B = [b_{C1}, b_{C2}, b_{C3}, b_{C4}, b_{C5}, b_{C6+}, b_{CO2}]$$

$$b_i = [b_i(\lambda_1), b_i(\lambda_2), \ldots, b_i(\lambda_m)]^T \quad (3)$$

In equation 3, $b_i$ represents a vector for each component (e.g., i=C1, C2, C3, C4, C5, C6+ and CO2) of the formation fluid. The prediction of the relative concentration for each component of the formation fluid may be used to determine the composition of the formation fluid in terms of weight fractions according to the following equations:

$$(\omega_{C1}, \omega_{C2}, \omega_{C3}, \omega_{C4}, \omega_{C5}, \omega_{C6+}, \omega_{CO2}) = \frac{y}{y_{total}} \quad (4)$$

$$y_{total} = \sum_i y_i \quad (5)$$

In equation 4, $\omega_i$ denotes the weight fraction of composition for component i. According to equations 4 and 5, the weight fraction for each component may be obtained by dividing the relative concentration for one component by the sum of the relative concentrations for all of the multiple components that make up the formation fluid.

Figure 5:
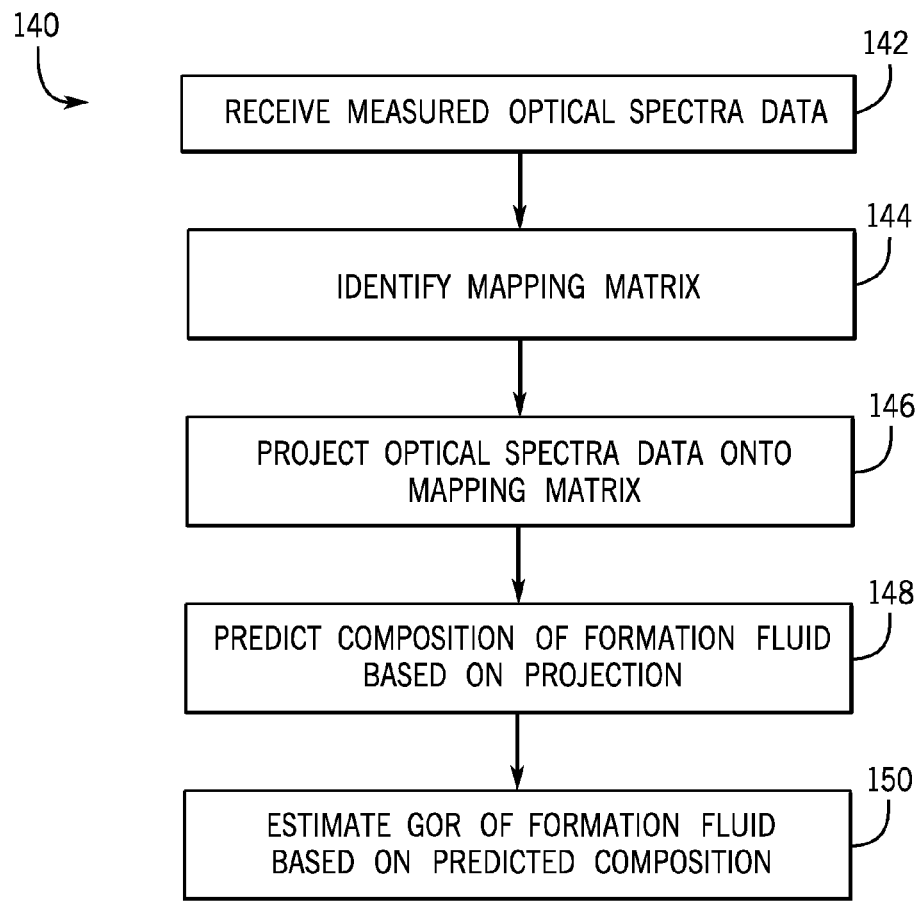
FIG. 5 is a process flow diagram of a method for predicting properties of the formation fluid flowing through the downhole equipment of FIG. 2, in accordance with an embodiment of the present techniques.

FIG. 5 is an embodiment of a method 140 for predicting (e.g., via applying the above equations 2-5) a parameter corresponding to one or more components of the formation fluid flowing through the downhole tool 50. The illustrated method 140 may represent one way of performing the parameter prediction outlined in block 134 of FIG. 4. It should be noted that the method 140 may be implemented as a computer or software program (e.g., code or instructions) that may be executed by the processor 100 to execute one or more parts of the method 140. Additionally, the program (e.g., code or instructions) may be stored in any suitable article of manufacture that includes at least one tangible non-transitory, computer-readable medium that at least collectively stores these instructions or routines, such as a memory or storage component of the control/monitoring system 90. The term non-transitory merely indicates that the medium is not a signal.

The method 140 includes receiving (block 142) the optical spectra data x from the spectrometer 72 of the downhole tool 50. This optical spectra data may include an optical density measured at each of the wavelengths λ of the detector 94. The method 140 may include identifying (block 144) a mapping matrix B for predicting certain formation fluid properties. In some embodiments, identifying (block 144) the mapping matrix may involve selecting an appropriate mapping matrix from a set of available mapping matrices, based on the received optical spectra data. For example, in some embodiments, a different mapping matrix may be used for different types of formation fluids flowing through the downhole tool 50. These different types of formation fluid include gas, gas condensate, and oil. The processor 100 may analyze the optical spectra data to determine the type of formation fluid and select the corresponding mapping matrix. Additional details relating to identifying the formation fluid type are described in PCT Application Serial No. PCT/US2013/030637, entitled "METHOD AND APPARATUS FOR IDENTIFYING FLUID ATTRIBUTES," to Indo et al., filed on Mar. 13, 2013, with priority to Provisional Application No. 61/666,593, filed Jun. 29, 2012, which are incorporated into the present disclosure by reference. Other methods may be used to identify the appropriate mapping matrix as well.

The method 140 also includes projecting (block 146) the optical spectra data onto the mapping matrix B (e.g., according to equation 2 above). The term projecting (or "projection") may refer to a linear transformation of the optical spectra data x onto the mapping matrix B. In addition, the method 140 may include predicting (block 148) a composition of the formation fluid flowing through the downhole tool 50 based on the projection. This composition may be expressed as relative concentrations (using equation 2) or weight fractions (using equations 4 and 5). Additional details relating to estimating the composition of the formation fluid from optical spectra data are described in U.S. patent application Ser. No. 13/644,772, entitled "DETERMINING FLUID COMPOSITION DOWNHOLE FROM OPTICAL SPECTRA," to Indo et al., filed on Oct. 4, 2012, which is incorporated into the present disclosure by reference. The method 140 may further include estimating (block 150) additional parameters, such as GOR of the formation fluid, based on the predicted composition. The processor 100 may be used to determine uncertainties in predictions of the composition for one or more components of the formation fluid, and to determine uncertainties in other parameters (e.g., GOR) derived from the composition.

There may be multiple sources of uncertainty involved in predicting the formation fluid composition from the optical spectra data. These sources may include methodological uncertainty, systematic uncertainty, and measurement noise, among others. Methodological uncertainty is related to errors in the calibration dataset stored within the database 104. That is, the compositions determined in the laboratory may contain errors and/or the corresponding optical spectra determined via the spectrometer 72 may contain errors. In addition, the methodological errors may include errors in deriving the mapping matrix B from the calibration dataset. Furthermore, the prediction may be based on a linear model (e.g., equation 2), while the actual relationship between the x and y values may be non-linear. Other sources of uncertainty associated with the prediction model may exist as well.

Systematic uncertainty may include errors that exist within the spectrometer 72 or other drilling system components, as opposed to within the prediction model. Such systematic uncertainty may be due to calibration error or wavelength error within the spectrometer 72. Measurement noise may represent the noise in the optical spectra data signal between the spectrometer 72 and the processor 100, or noise in signals communicated between different processing components of the control/monitoring system 90.

The obtained optical spectrum x and the predicted parameter y may be defined in terms of expected values ($\bar{x}$, $\bar{y}$) and their errors ($\Delta x$, $\Delta y$). In the same manner, the expected value of a mapping matrix and its error may be described using $\bar{B}$ and $\Delta B$, respectively:

$$x = \bar{x} + \Delta x$$

$$y = \bar{y} + \Delta y$$

$$B = \bar{B} + \Delta B \quad (6)$$

In equation 6, $\bar{x}$ may include unknown systematic errors (e.g. baseline errors, temperature drift and/or wavelength errors), while $\Delta x$ may include uncertainty due to measurement noise. The error in B, $\Delta B$ may include methodological uncertainties (e.g. errors in the database 104, calibration errors, non-linearity in the model, etc.). Accordingly, for any one of the individual components i=C1, C2, C3, C4, C5, C6+, and CO2, equation 2 may be combined with equation 6 to write:

$$\bar{y}_i + \Delta y_i = (\bar{x} + \Delta x)(\bar{b}_i + \Delta b_i) = \bar{x}\bar{b}_i + \bar{x}\Delta b_i + \Delta x \bar{b}_i + \Delta x \Delta b_i \text{ or}$$

$$\Delta y_i \approx \bar{x} \Delta b_i + \Delta x \bar{b}_i$$

under the assumption that $\Delta x \Delta b_i \ll \bar{x} \Delta b_i$ and
$\Delta x \Delta b_i \ll \Delta x \bar{b}_i$ \quad (7)

The uncertainty in the predicted parameter $\bar{y}_i$ may be expressed in terms of the standard deviation which is the square root of the variance of $\Delta y_i$. The variance of $\Delta y_i$ is given by the expression below:

$$\text{var}(\Delta y_i) = E\left((\bar{x}\Delta b_i + \Delta x \bar{b}_i)(\bar{x}\Delta b_i + \Delta x \bar{b}_i)^T\right) \quad (8)$$

$$= E(\bar{x}\Delta b_i \Delta b_i^T \bar{x}^T + \Delta x \bar{b}_i \bar{b}_i^T \Delta x^T +$$

$$\bar{x}\Delta b_i \bar{b}_i^T \Delta x^T + \Delta x \bar{b}_i \Delta b_i^T \Delta \bar{x}^T)$$

$$= \bar{x}\text{cov}(\Delta b_i)\bar{x}^T + \bar{b}_i^T \text{cov}(\Delta x)\bar{b}_i + 2E(\bar{x}\Delta b_i \Delta x \bar{b}_i)$$

In equation 8, the function E, applied to a variable, denotes an expected value of that variable. Terms such as $b_i b_{i.}^T$, with or without the $\Delta$s, are generally interpreted as tensor (ie., dyadic) products. The last term of the last line of equation 8 may be eliminated under the assumption that the errors in the columns of the mapping matrix and the errors in the optical spectra are uncorrelated and, further, that the expected value of the measurement error (for example, noise), $E(\Delta x)$, is assumed to be approximately equal to zero, that is $$E(\bar{x}\Delta b_i \Delta x \bar{b}_i) = \bar{x} E(\Delta b_i) E(\Delta x) \bar{b}_i \approx 0 \text{ since } E(\Delta x) \approx 0 \quad (9)$$

Thus, the resulting uncertainty in the prediction of y is approximated as the square root of the variance of $\Delta y_1$, as shown below:

$$(\text{var}(\Delta y_i))^{1/2} \approx (\bar{x} \text{cov}(\Delta b_i)\bar{x}^T + \bar{b}_i^T \text{cov}(\Delta x)\bar{b}_i)^{1/2} \quad (10)$$

In equation 10, the covariance of $\Delta b_i$ may be predetermined from the calibration dataset stored in the database 104, and $\text{cov}(\Delta x)$ may be determined using the optical spectra data collected in real-time.

Figure 6:
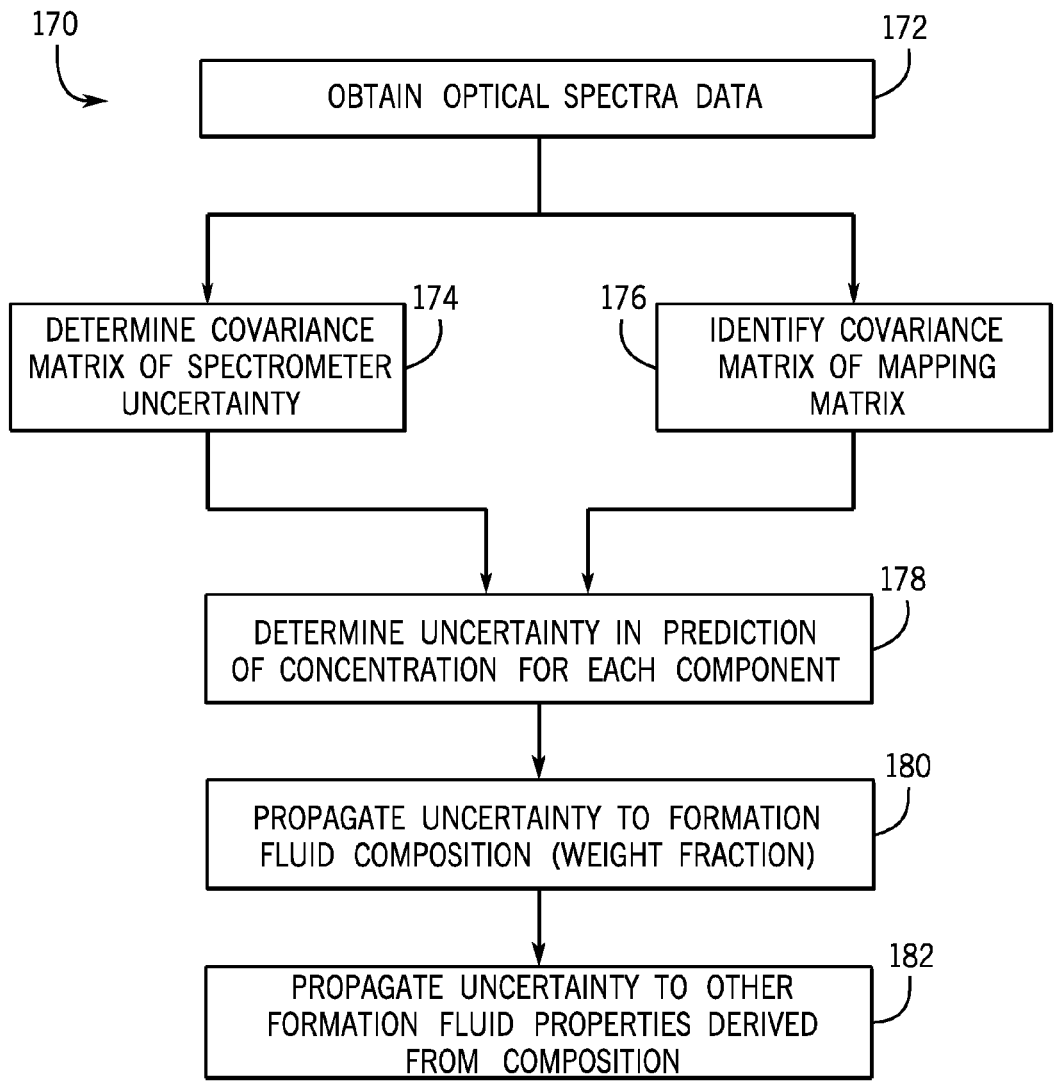
FIG. 6 is a process flow diagram of a method for determining uncertainties of the properties predicted via the method in FIG. 5, in accordance with an embodiment of the present techniques.

FIG. 6 is a process flow diagram of a method 170 for determining uncertainties of the predicted parameters (e.g., composition, GOR) of the formation fluid. The illustrated method 170 may represent one way of performing the uncertainty determination outlined in block 136 of FIG. 4. Similar to the method 140, the method 170 may be performed via the processor 100, which includes one or more processors throughout the drilling system 10. The method 170 includes obtaining (block 172) the optical spectra data from the spectrometer 72. The method 170 also includes determining (block 174) the covariance matrix $\text{cov}(\Delta x)$ of measurement uncertainty in the spectrometer 72, derived from the obtained optical spectra data. This block 174 may represent a determination of noise in the optical spectra data signal, as outlined below in FIG. 7.

In addition, the method 170 may include identifying (block 176) the covariance matrix $\text{cov}(\Delta b_i)$ of the mapping matrix B. This covariance matrix $\text{cov}(\Delta b_i)$ may be derived from the calibration dataset stored in the database 104. The covariance matrix may be selected from a set of covariance matrices corresponding to different mapping matrices that may be applied to the optical spectra data. As described above with reference to FIG. 5, the mapping matrix B may be identified based on the type of formation fluid flowing through the downhole tool 50, and this formation fluid type may be determined based on the obtained optical spectra data. Similarly, the covariance matrix of the mapping matrix may correspond to a particular type of formation fluid, which is determined based on the optical spectra data.

The derivation of the covariance matrix $\text{cov}(\Delta b_i)$ and the mapping matrix B from the calibration dataset may be accomplished once for each type of fluid during an initial calibration of the downhole tool 50, and then used in uncertainty determinations for each spectrum taken thereafter. In embodiments where the dataset is updated based on laboratory results, the derivation may be performed again when changes are made to the database 104.

Any number of methods may be used to derive the uncertainty (e.g., covariance matrix) of the mapping matrix based on the calibration data available in the database 104. In some embodiments, it may be desirable to use statistical methods that do not assume an underlying probability distribution of the calibration dataset. For example, one possible way to determine the covariance of the mapping matrix includes applying a bootstrapping method to the calibration dataset. The term "bootstrapping method" refers to a statistical method that uses random resampling of a population, with replacement. The bootstrapping method may derive statistical measures from the replicated samples following the statistical distribution of the population. More specifically, several mapping matrices B may be replicated from randomly resampled datasets within the database 104. Each of the datasets may be calibrated according to the same calibration model. From the replicated mapping matrices, a processor may determine a matrix element $(\lambda, \lambda')$ of the covariance matrix $cov(\Delta b_i)$ according to the following equations:

$$cov(\Delta b_i)_{\lambda \lambda'} = \frac{1}{N} \sum_{k=1}^{N} \left( b_i^{(k)}(\lambda) - \bar{b}_i(\lambda) \right)\left( b_i^{(k)}(\lambda') - \bar{b}_i(\lambda') \right) \quad (11)$$

$$\bar{b}_i(\lambda) = \frac{1}{N} \sum_{k=1}^{N} b_i^{(k)}(\lambda) \quad (12)$$

In equations 11 and 12, $b_i^{(k)}(\lambda)$ represents the element $\lambda$ in the column vector i of the $k^{th}$ replicated mapping matrix, $B^{(k)}$. The indices $\lambda$ and i are, respectively, associated with wavelength channel and a component of interest (C1, C2, C3, C4, C5, C6+ and CO2). N is the total number of replications of the mapping matrix generated by the bootstrapping method.

In the method 170, the two derived covariance matrices ($cov(\Delta x)$ and $cov\Delta b_i$) may be used to determine (block 178) the uncertainty in the prediction of a concentration for each formation fluid component. This predicted concentration may be a relative concentration (e.g., y from equation 2 above), and the uncertainty in this prediction may be expressed as a standard deviation (that is, the square root of the variance) of y. Equation 10 shows one example of the uncertainty calculation, which is based on the covariance matrix $cov(\Delta x)$ of the measured data and the covariance matrix $cov(\Delta b_i)$ of the mapping matrix. In addition, Equation 10 is based on $\bar{b}_i$, which may be determined via Equation 12, and $\bar{x}$, which may be obtained by filtering and smoothing the optical spectra data, as shown below. Using equation 10, the processor 100 may determine the uncertainty in predicting a parameter of one of the multiple components i of the formation fluid based on a calculated uncertainty in the optical spectra data and based on an identified uncertainty in the calibration dataset. In other embodiments, the specific equations governing the determination of the uncertainty in the predicted parameter may be different.

The determined uncertainty may be for a predicted parameter of a single formation fluid component. However, if such uncertainties are determined for each component of the formation fluid, these may be used to determine uncertainties of parameters of the formation fluid as a whole. In some embodiments, the method 170 may include propagating the uncertainty in the predicted relative concentration determined for each individual component to other parameters, as shown in blocks 180 and 182. More specifically, the method 170 may include propagating (block 180) the uncertainty to formation fluid composition in weight fraction. Formation fluid composition may include a weight percentage for each of the components that make up the formation fluid. As discussed above with reference to equations 4 and 5, this weight fraction may be determined as follows:

$$\omega_i = f_i(y_{C1}, y_{C2}, y_{C3}, y_{C4}, y_{C5}, y_{C6+}, y_{CO2}) = \frac{y_i}{\Sigma_j y_j} \quad (13)$$

$(i, j = C1, C2, C3, C4, C5, C6+, CO2)$

The uncertainty or error in the weight fraction may be propagated from the error in the relative concentrations of the formation fluid components:

$$\Delta \omega_i \cong \Sigma_j \frac{\partial f_i}{\partial y_j} \Delta y_j \quad (14)$$

Subsequently, the variance of $\Delta \omega_i$ may be obtained as follows:

$$var(\Delta \omega_i) \cong \Sigma_j \Sigma_k \frac{\partial f_i}{\partial y_j} \frac{\partial f_i}{\partial y_k} \Delta y_j \Delta y_k = \quad (15)$$

$$\frac{\Delta y_i^2}{(\Sigma_j y_j)^2} - \frac{2 y_i \Delta y_i \Sigma_j \Delta y_j}{(\Sigma_j y_j)^3} + \frac{y_i^2 (\Sigma_j \Delta y_j)^2}{(\Sigma_j y_j)^4}$$

The uncertainty in the weight fraction for any one of the multiple components of the formation fluid may be determined as the square root of the variance calculated in equation 15. Thus, upon prediction of the relative concentrations for each of the formation fluid components and determination of the uncertainty for each respective component, the uncertainty for the weight fraction may be determined as well. This uncertainty may be expressed as a confidence interval (e.g., 68%, 95%) for the predicted weight fraction.

In addition to propagating (block 180) the uncertainty to weight fraction, the method 170 may include propagating (block 182) the uncertainty to additional formation fluid properties. These other properties may be derived from the formation fluid composition (e.g., weight fraction) as shown below:

$$F = F(\omega_{C1}, \omega_{C2}, \omega_{C3}, \omega_{C4}, \omega_{C5}, \omega_{C6+}, \omega_{CO2}) \quad (16)$$

The error in calculating F based on the predicted weight fractions may be expressed as follows:

$$\Delta F \cong \sum_j \frac{\partial F}{\partial \omega_j} \Delta \omega_j \quad (17)$$

In cases where the property is defined by an algorithm rather than an explicit relation in terms of the weight fractions, for example GOR, the partial derivative of F with respect to $\omega_j$ can be computed numerically:

$$\frac{\partial F}{\partial \omega_j} = \frac{1}{2\varepsilon} [F(\omega_{C1}, \omega_{C2}, \ldots, \omega_j + \varepsilon, \ldots, \omega_{CO2}) - \quad (18)$$

$$F(\omega_{C1}, \omega_{C2}, \ldots, \omega_j - \varepsilon, \ldots, \omega_{CO2})]$$

where j=C1, C2, C3, C4, C5, C6+ or CO2 and $\varepsilon$ is a small number larger than machine The variance of F is provided according to the equation below:
precision.

$$\text{var}(\Delta F) \cong \sum_j \sum_k \frac{\partial F}{\partial \omega_j} \frac{\partial F}{\partial \omega_k} \Delta\omega_j \Delta\omega_k \quad (19)$$

As an example, the uncertainty in weight fraction calculations may be propagated (block 182) according to equation 19 to a predicted GOR of the formation fluid. In general, the GOR is a function of the weight fractions for various components of the formation fluid as follows:

$$GOR = GOR(\omega_{C1}, \omega_{C2}, \omega_{C3-5}, \omega_{C6+}, \omega_{CO2}) \quad (20)$$

According to equation 20, GOR is a function of certain groupings of the components that make up the formation fluid: C1, C2, C3-5, C6+, and CO2. By applying equation 19, the uncertainty in the calculated GOR may be determined as follows, where j and k represent each of the five formation fluid component groups:

$$\text{var}(\Delta GOR) \cong \sum_j \sum_k \frac{\partial GOR}{\partial \omega_j} \frac{\partial GOR}{\partial \omega_k} \Delta\omega_j \Delta\omega_k \quad (21)$$

One sigma confidence interval of the predicted GOR may be given as the square root of the variance var($\Delta GOR$) calculated via equation 21. Equation 19 may be used to determine uncertainty in other parameters derived from the calculated weight fraction for one or more components of the formation fluid.

Figure 7:
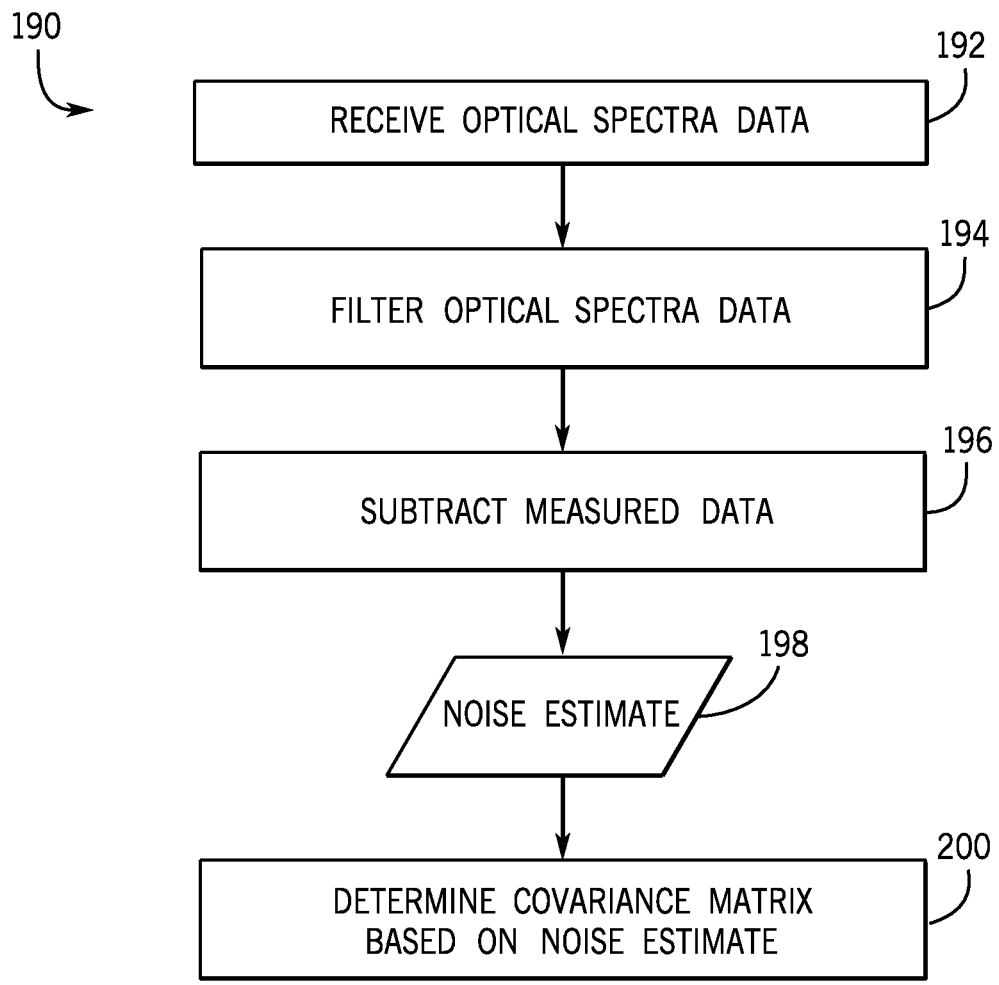
FIG. 7 is a process flow diagram of a method for performing part of the uncertainty determination of FIG. 6, in accordance with an embodiment of the present techniques.

FIG. 7 is a process flow diagram of an embodiment of a method 190 that provides one way to determine (block 174) the covariance matrix cov($\Delta x$) of uncertainty in the optical spectra data and another term $\bar{x}$ used to calculate the overall uncertainty associated with the predicted parameters. It should be noted that the method 190 may be implemented as a computer or software program (e.g., code or instructions) that may be executed by the processor 100 to execute one or more parts of the method 190. Additionally, the program (e.g., code or instructions) may be stored in any suitable article of manufacture that includes at least one tangible non-transitory, computer-readable medium that at least collectively stores these instructions or routines, such as a memory or storage component of the control/monitoring system 90. The term non-transitory merely indicates that the medium is not a signal.

The method 190 includes receiving (block 192) the optical spectra data from the spectrometer 72 and filtering (block 194) the optical spectra data to generate filtered optical spectra data. This filtered optical spectra data is the $\bar{x}$ of equation 10. In addition, the method 190 includes subtracting (block 196) the measured optical spectra data from the filtered optical spectra data to generate a noise estimate 198. Further, the method 190 includes determining (block 200) the covariance matrix cov($\Delta x$) based on the noise estimate 198.

The filtering (block 194) may involve fitting the optical spectra data within an appropriate time window according to a certain type of function. For example, the optical density may be collected at each wavelength over a period of time, and the data may be fitted locally at multiple points within the time period according to a quadratic function. Subtracting (block 196) the filtered optical density from the raw optical density may yield an estimate of the local noise within the signal at a particular time t. From the noise in the channels (e.g., at each wavelength of the spectrometer 72), the matrix elements of cov($\Delta x$) may be determined. These elements may represent the covariance of the optical density noise (i.e., measurement noise) present at a given time t according to the following equations:

$$\text{cov}(\Delta x)_{\lambda\lambda'} = \frac{1}{M} \sum_{T=t-t_w}^{t+t_w} \Delta x_T(\lambda) \Delta x_T(\lambda') \quad (22)$$

$$\Delta x(\lambda) = [\Delta x_{t-t_w}(\lambda), \Delta x_{t-t_w+1}(\lambda), \quad (23)$$
$$\ldots, \Delta x_t(\lambda), \ldots, \Delta x_{t+t_w-1}(\lambda), \Delta x_{t+t_w}(\lambda)]$$

In equation 22, $\lambda$ and $\lambda'$ serve as indices identifying a particular element in the covariance matrix of $\Delta x$. The covariance matrix of $\Delta x$ at time t may be determined within the time window (t−$t_w$≤T≤t+$t_w$), centered at time t. In equation 22, M is the number of points within the time window. Other methods not discussed herein may be used to determine the covariance matrix of $\Delta x$ based on the measured optical spectra data.

Figure 8:
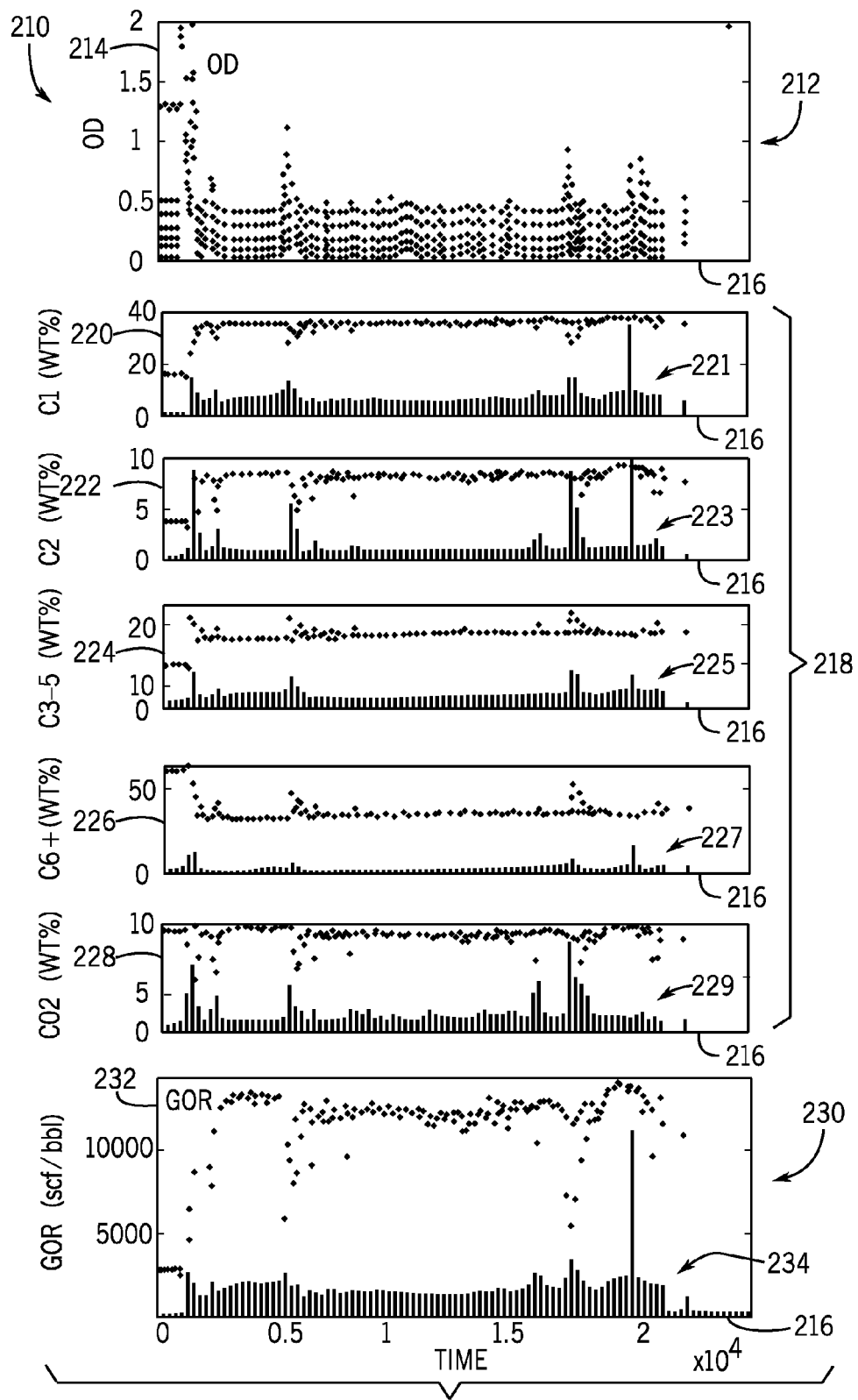
FIG. 8 is a series of subplots representative of optical density measurements, composition predictions, and GOR predictions made in accordance with an embodiment of the present techniques.

FIG. 8 is an array of subplots 210 illustrating an example of various predicted parameters and their associated uncertainties determined using the method 170. An optical spectra data subplot 212 shows the optical density 214, as detected by the spectrometer 72, with respect to time 216. The optical spectra data subplot 212 includes multiple data points collected at each time, these data points corresponding to 6 of the 20 different wavelengths acquired during sampling of the formation fluid. In the illustrated embodiment, the formation fluid is a gas condensate. Other types of formation fluid include gas and crude oil, and different calibration models may be used to predict the composition of these different types of formation fluid.

From the optical density data in the optical spectra data subplot 212, the processor 100 may predict the relative concentrations and, subsequently, the weight fraction of one or more components that make up the formation fluid. A set of five weight fraction subplots 218 illustrate these predictions and their associated uncertainties. For example, one subplot 218 shows the weight fraction 220 of C1 (as a percentage) with respect to time 216. Similarly, the subplots 218 include the predicted weight fractions 222, 224, 226, and 228 of C2, C3-5, C6+, and CO2, respectively. In some embodiments, the disclosed techniques may be used to predict the weight fractions (and determine the uncertainty in such predictions) of C3, C4, and C5 individually, as opposed to in a single grouping as shown. In the illustrated embodiment, an upper portion of each subplot 218 shows the predicted weight fraction for the corresponding component. These weight fractions may be predicted according to equations 2-5, as discussed above. In addition, the positive portions of the error bars 221, 223, 225, 227, and 229 are included along the lower portion of each subplot 218, illustrating the uncertainty in the predicted weight fractions 220, 222, 224, 226, and 228, respectively. These error bars 221, 223, 225, 227, and 229 may be determined according to equation 10 above. As illustrated, the error bars may differ in size and arrangement for each component of the formation fluid. This indicates that different amounts and types of error may be present in the predictions for the different formation fluid components.

Based on the predicted weight fractions 220, 222, 224, 226, and 228, the processor 100 may predict the GOR of the formation fluid. In the illustrated embodiment, a GOR subplot 230 shows predicted values of the GOR 232 of the formation fluid with respect to time 216. The GOR 232 may be estimated from the weight fractions 220, 222, 224, 226, and 228 according to equation 20. The GOR subplot 230 also includes error bars 234 propagated from the weight fraction errors for the individual components C1, C2, C3-5, C6+, and CO2. The uncertainty in the GOR may be calculated according to equation 21 above. By using the calculations and methods described herein, present embodiments allow for the quantitative determination of uncertainty in predicted parameters for one or more components of the formation fluid, and the propagation of such uncertainty to aggregate parameters of the formation fluid, such as GOR. Such uncertainty determinations may provide reliable indicators of the accuracy in formation fluid parameter predictions.

Figure 9:
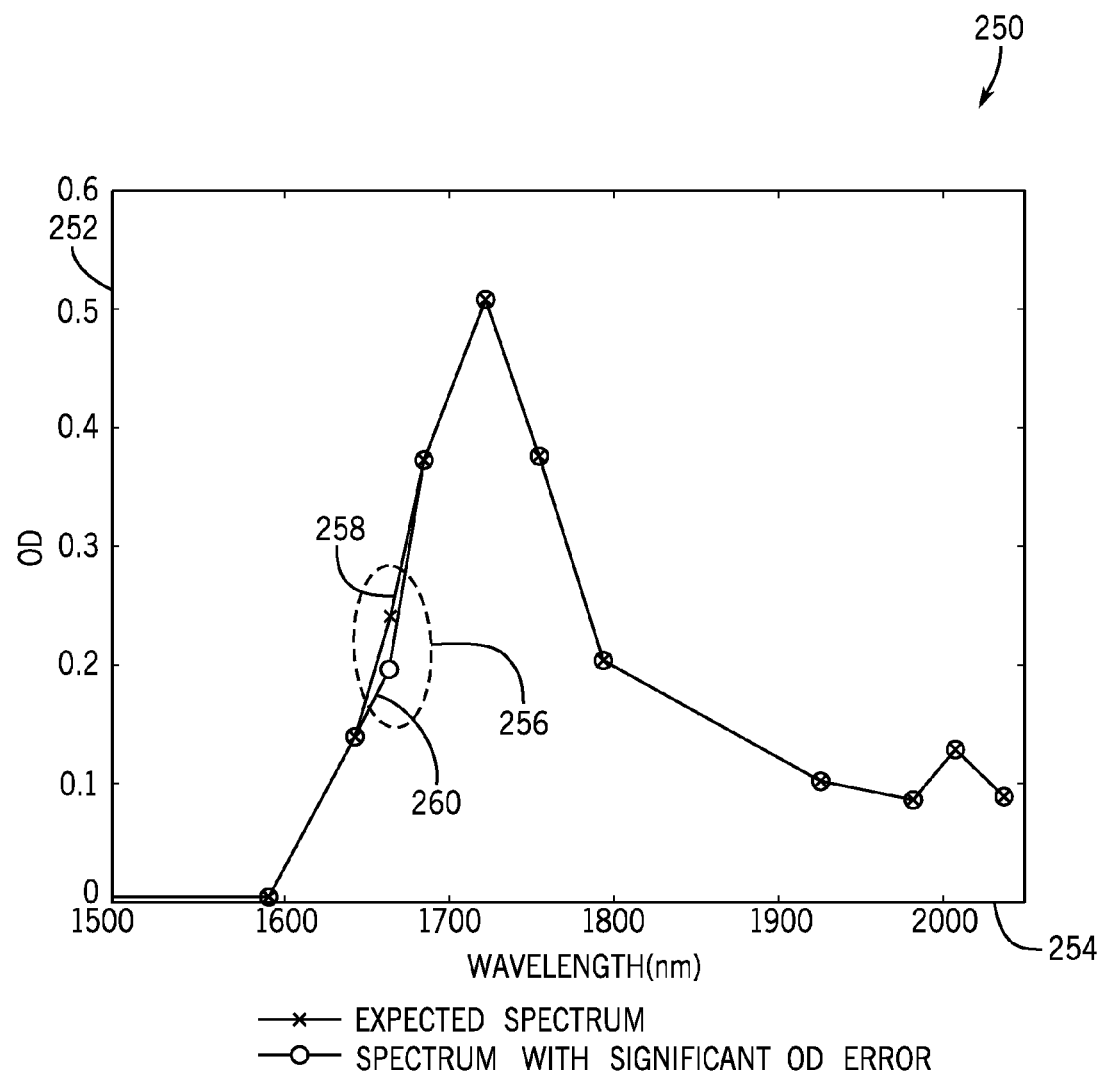
FIG. 9 is a plot representative of a measured optical density of formation fluid taken with respect to wavelength via a spectrometer, in accordance with an embodiment of the present techniques.

In addition to providing quantitative measures of prediction uncertainty, the processor 100 may be configured to diagnose an operational issue in the downhole tool 50 based on the calculated uncertainty. This operational issue may include a malfunction in one or more of the detector elements 98 in the spectrometer 72. An example of this diagnosis is illustrated in FIG. 9, which shows a plot 250 of optical density 252 taken with respect to wavelength 254. The wavelengths 254 shown in the plot 250 are within a near infrared (NIR) region. In the illustrated embodiment, the optical spectrum has relatively large optical density error at one of the wavelength channels (e.g., 1671 nm). This error is indicated via a dashed circle 256, where expected values 258 of the optical spectra data diverge from an optical spectra data measurement 260 obtained via the spectrometer 72. The expected spectrum 258 represents the optical spectrum that would likely be measured if no issues were present within the spectrometer 72.

Parameters of the individual components of the formation fluid, as well as aggregate parameters of the formation fluid, may be determined based on the measured optical spectrum 260 of FIG. 9. Table 1 below shows these predicted parameters and their associated uncertainties, which may be calculated via the processor 100 according to one or more of the methods discussed above. These predicted parameters include, for example, the composition and GOR of the formation fluid. The predicted parameters and associated uncertainties are also shown for the expected spectrum 258 of FIG. 9.

TABLE 1

| Crude Oil | C1 (wt %) | C2 (wt %) | C3-5 (wt %) | C6+ (wt %) | CO2 (wt %) | GOR (scf/bbl) |
|---|---|---|---|---|---|---|
| Expected spectrum | | | | | | |
| Prediction | 16.0 | 3.7 | 10.4 | 60.4 | 9.4 | 2930 |
| C.I. (95%) | +/−2.0 | +/−0.8 | +/−3.6 | +/−3.2 | +/−0.8 | +/−300 |
| Spectrum with an error | | | | | | |
| Prediction | 16.3 | 6.4 | 17.6 | 48.8 | 10.9 | 4200 |
| C.I. (95%) | +/−10.4 | +/−3.4 | +/−7.4 | +/−29.4 | +/−8.4 | +/−2200 |
| PVT Laboratory | | | | | | |
| Lab (GC) | 15.2 | 4.8 | 11.3 | 59.8 | 8.6 | 2820 |

As shown in table 1, the predicted parameters determined based on the erroneous measurement data (spectrum with error) differ greatly from the results determined in the laboratory. However, the uncertainties (95% confidence intervals) determined for the parameters predicted from the erroneous spectrum are relatively high compared to those determined for the expected spectrum. If one or two of the predicted parameters were determined with relatively high uncertainties, this may indicate that the model (e.g., mapping matrix B) used in the prediction contains errors. However, since the predicted parameters in Table 1 feature relatively high uncertainties, this may indicate that the predicted parameters are subject to uncertainty caused by system errors. Thus, the relatively high uncertainties determined for a number of predicted parameters may alert an operator to operational issues within the spectrometer 72 or other components of the downhole tool 50.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A system, comprising:
    a downhole formation fluid sampling tool;
    an optical spectrometer of the downhole formation fluid sampling tool, wherein the optical spectrometer is configured to measure an optical characteristic of a formation fluid flowing through the downhole formation fluid sampling tool over a plurality of wavelengths and configured to generate optical spectra data indicative of the optical characteristic, wherein the formation fluid comprises multiple components; and
    a processor configured to receive the optical spectra data generated by the optical spectrometer, to predict a parameter corresponding to one component of the multiple components of the formation fluid based on the optical spectra data including transforming the optical spectra data according to a set of mapping values, and to calculate a quantitative uncertainty in the predicted parameter based on the optical spectra data based on a set of covariance values corresponding to the set of mapping values or based on a set of covariance values corresponding to the obtained optical spectra data or both.

2. The system of claim 1, wherein the processor is configured to:
    predict the parameter corresponding to one or more components of the formation fluid by fitting the optical spectra data to a model, the model being derived from a calibration dataset stored in a database, wherein the model includes the set of mapping values;
    determine a quantitative measurement uncertainty in the received optical spectra data based on the set of covariance values corresponding to the obtained optical spectra data;
    identify a quantitative model uncertainty in the model derived from the calibration dataset, wherein the quantitative model uncertainty is based on the set of covariance values corresponding to the set of mapping values; and
    determine the quantitative uncertainty in the predicted parameter based on the quantitative measurement uncertainty and the quantitative model uncertainty.

3. The system of claim 1, wherein the parameter corresponding to the one component of multiple components of the formation fluid comprises a concentration of the one component in the formation fluid.

4. The system of claim 1, wherein the processor is configured to:
    estimate a property of the formation fluid based on respective predicted parameters for the multiple components of the formation fluid;

calculate quantitative uncertainties in predicting the respective parameters for the multiple components; and calculate a quantitative uncertainty of the estimated property of the formation fluid based on the calculated quantitative uncertainties in predicting the respective parameters.

5. The system of claim 3, wherein the estimated property of the formation fluid comprises a gas to oil ratio (GOR) of the formation fluid.

6. The system of claim 1, wherein the processor is configured to diagnose an operational issue in the downhole formation fluid sampling tool based on the calculated quantitative uncertainty.

7. The system of claim 1, wherein the processor is configured to determine a confidence interval of the predicted parameter based on calculating the quantitative uncertainty.

8. The system of claim 1, wherein the optical characteristic comprises an optical density of the formation fluid at the plurality of wavelengths.

9. The system of claim 1, wherein the downhole formation fluid sampling tool is disposed within a wellbore extending into a formation, via a wireline or a string of tubulars.

10. A method, comprising:
receiving optical spectra data into a processor, the optical spectra data being representative of optical characteristics of a formation fluid, wherein the formation fluid comprises multiple components;
predicting, via the processor, a parameter corresponding to one component of the multiple components of the formation fluid based on the optical spectra data, wherein the prediction includes transforming the optical spectra data according to a set of mapping values; and
determining, via the processor, a quantitative uncertainty in the predicted parameter corresponding to the one component of the multiple components of the formation fluid based on the optical spectra data based on a set of covariance values corresponding to the set of mapping values or based on a set of covariance values corresponding to the obtained optical spectra data or both.

11. The method of claim 10, comprising predicting the parameter by fitting the optical spectra data to a model, the model being derived from a calibration dataset stored in a database, wherein the model includes the set of mapping values.

12. The method of claim 11, comprising:
identifying a quantitative model uncertainty corresponding to the model, wherein the quantitative model uncertainty is derived from the calibration dataset including by determining the set of covariance values corresponding to the set of mapping values from the calibration dataset;
determining a quantitative measurement uncertainty derived from a measurement of the optical spectra data including determining the set of covariance values corresponding to the obtained optical spectra data; and
determining the quantitative uncertainty in the predicted parameter based on the quantitative model uncertainty and the quantitative measurement uncertainty.

13. The method of claim 12, wherein the model comprises a mapping matrix that includes the set of mapping values, wherein predicting the parameter comprises performing a linear transformation of the optical spectra data according to the mapping matrix, and wherein the quantitative model uncertainty is based on a covariance matrix of the mapping matrix that includes the set of covariance values corresponding to the set of mapping values.

14. The method of claim 10, comprising determining a quantitative uncertainty in predicting an aggregate parameter corresponding to the formation fluid, based on the calculated quantitative uncertainty of the parameter corresponding to the one component.

15. The method of claim 10, comprising predicting the parameter and determining the quantitative uncertainty in the predicted parameter, while the formation fluid is flowing through a downhole formation fluid sampling tool.

16. A method, comprising:
receiving optical spectra data into a processor, the optical spectra data being representative of optical characteristics of a formation fluid flowing through the downhole formation fluid sampling tool, wherein the formation fluid comprises one or more components;
predicting, via the processor, a parameter corresponding to the one or more components of the formation fluid based on the optical spectra data and a model derived from a calibration dataset, wherein the model comprises a set of mapping values;
determining, via the processor, a quantitative measurement uncertainty in the received optical spectra data including determining a set of covariance values corresponding to the obtained optical spectra data;
identifying, via the processor, a quantitative model uncertainty in the model derived from the calibration dataset including by determining a set of covariance values corresponding to the set of mapping values derived from the calibration dataset; and
determining, via the processor, a quantitative uncertainty in the predicted parameter based on the quantitative measurement uncertainty and the quantitative model uncertainty.

17. The method of claim 16, wherein predicting the parameter corresponding to the one or more components of the formation fluid comprises determining a formation fluid type based on the optical spectra data and selecting the model corresponding to the determined formation fluid type.

18. The method of claim 16, comprising deriving the quantitative model uncertainty in the model by applying a bootstrapping method to the calibration dataset.

19. The method of claim 16, comprising updating the model with additional calibration data, wherein the additional calibration data is determined based in part on the optical spectra data.

20. The method of claim 16, wherein determining the quantitative measurement uncertainty comprises filtering the optical spectra data to generate filtered data, and subtracting the filtered data from the optical spectra data to obtain a measurement noise estimate.

* * * * *